United States Patent [19]

Clayman

[11] 4,298,994
[45] Nov. 10, 1981

[54] POSTERIOR CHAMBER INTRA-OCULAR TRANSPLANT DEVICE

[76] Inventor: Henry M. Clayman, 13255 Biscayne Bay Dr., Miami, Fla. 33181

[21] Appl. No.: 88,643

[22] Filed: Oct. 26, 1979

[51] Int. Cl.³ .............................. A61F 1/16; A61F 1/24
[52] U.S. Cl. ........................................................... 3/13
[58] Field of Search .............................................. 3/13

[56] References Cited

U.S. PATENT DOCUMENTS

| | | | |
|---|---|---|---|
| 3,866,249 | 2/1975 | Flom | 3/13 |
| 3,913,148 | 10/1975 | Potthast | 3/13 |
| 3,922,728 | 12/1975 | Krasnor | 3/13 |
| 4,056,855 | 11/1977 | Kelman | 3/13 |
| 4,073,014 | 2/1978 | Poler | 3/13 |
| 4,087,866 | 5/1978 | Choyce et al. | 3/13 |
| 4,159,546 | 7/1979 | Shearing | 3/13 |
| 4,174,543 | 11/1979 | Kelman | 3/13 |
| 4,214,585 | 7/1980 | Bailey, Jr. | 3/13 X |

FOREIGN PATENT DOCUMENTS

| | | | |
|---|---|---|---|
| 959314 | 3/1957 | Fed. Rep. of Germany | 3/13 |
| 1103399 | 5/1955 | France | 3/13 |

OTHER PUBLICATIONS

Jalie, M.; "The Design of Intra-ocular Lenses", article published by the British Optical Association, pp. 1–21, 5/1978.

Tennant; *A Lens for all Seasons* (Book), copyright 1976, pp. 46–51 and pp. 62, 63, 66, 67.

Primary Examiner—Clifford D. Crowder
Attorney, Agent, or Firm—Cushman, Darby & Cushman

[57] ABSTRACT

An intra-ocular implantable device and a method of surgically implanting such device in which upper and lower haptic loops are attached to a lens on opposite sides thereof for contacting the ciliary sulcus (or capsular bag) to position the lens in the posterior chamber. The lower loop has a stiffness greater than the upper loop and the lens has a vertical dimension greater than its horizontal dimension to ensure proper positioning of the lens. The lens has a rear convex surface for facilitating discission after implantation and optical advantages. Upper and lower bores in the front surface of the lens extend at an angle to the vertical of, for example, 15° to 20° to permit fixation by a fine spatula for manipulation of the device during implantation. The edges of the lens between the loops include straight line portions for guiding the device during insertion and requiring minimum incision.

13 Claims, 6 Drawing Figures

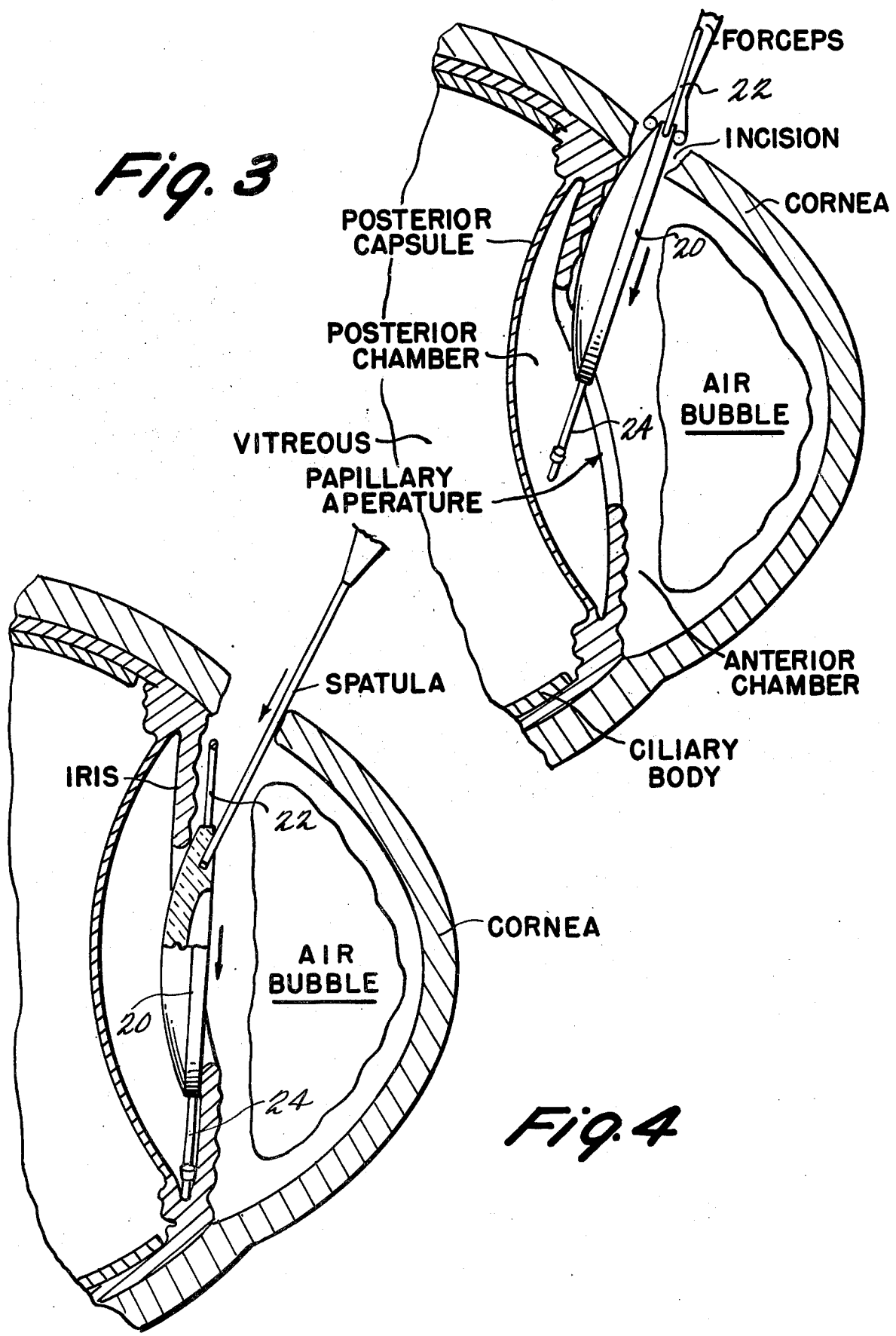

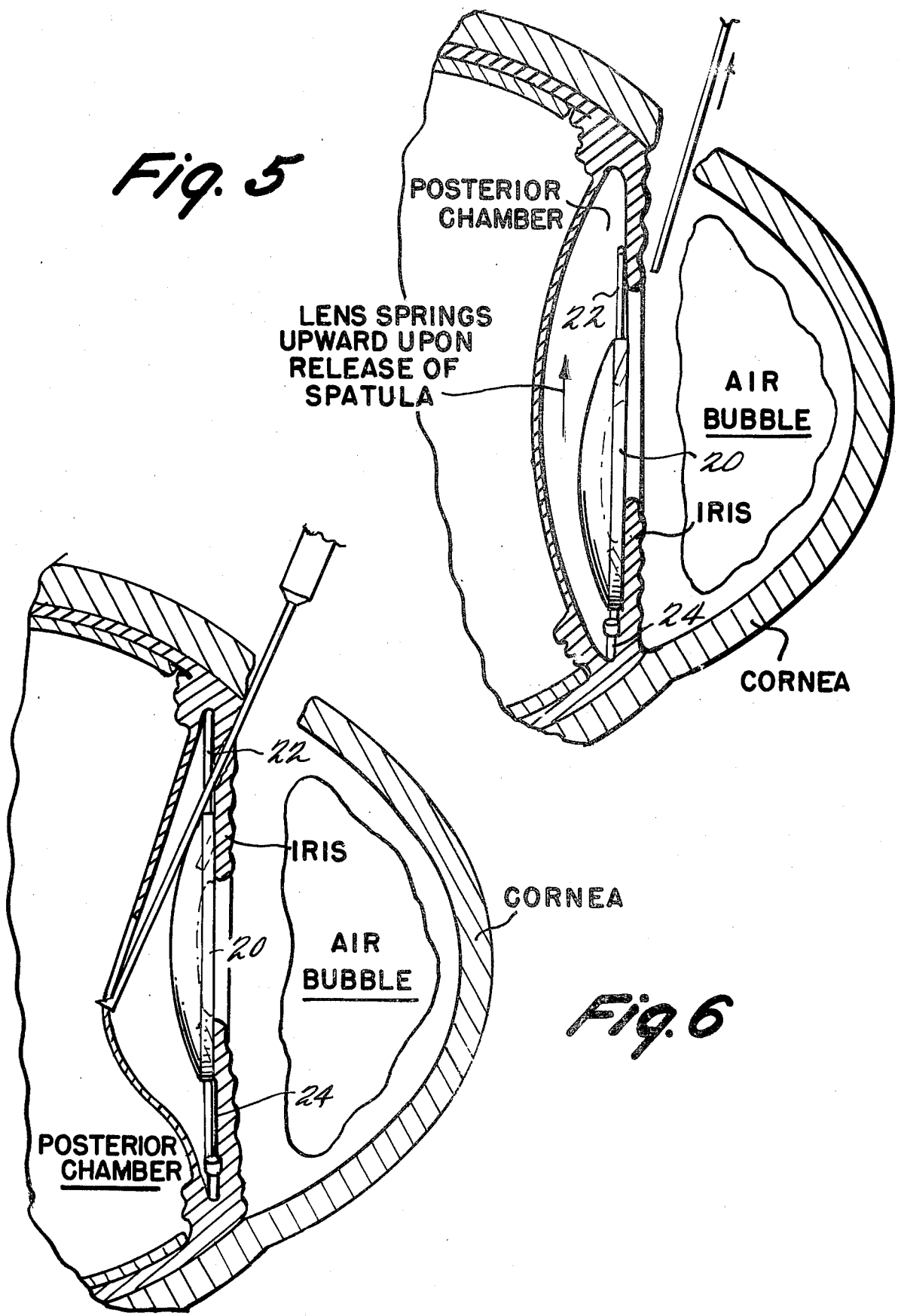

POSTERIOR CHAMBER INTRA-OCULAR TRANSPLANT DEVICE

BACKGROUND AND SUMMARY OF THE INVENTION

The invention relates to an intra-ocular implantable device and to a method of surgically implanting such device in the posterior chamber of a human eye.

Surgical removal of opaque lenses from the eyes of cataract patients is one of the most common surgical procedures. After such surgery, contact lenses or spectacles are usually prescribed to provide at least limited vision for the patient. While spectacle lenses and contact lenses have a number of optical drawbacks, the ready ability to remove or replace them if defective makes them safe and attractive appliances.

For some patients, however, spectacles and contact lenses are not workable. Many older patients are unable to insert and remove the contact lenses or even handle the thick spectacles. The same is true with very young patients. Fortunately for such patients a surgical alternative is available—implantation of a prosthetic or artificial lens into the interior of the eye to replace the opaque natural lens which has been surgically removed. While this type of surgery for all cataract patients may not be appropriate now, improvements in lenses and techniques, such as the present invention, may make such surgery universal for cataract patients in the future. This operation is called lens implant insertion and well over 100,000 such operations have taken place to date in the United States.

For first intra-ocular lens of modern times was implanted by Ridley in 1949 into the posterior chamber of an eye. Because of difficulties encountered with fixation in the posterior chamber, most implantations thereafter were in the anterior chamber or involved clipping in some fashion to the iris. *Pseudophakos*, by Jaffe, Galin, Hirschman, and Clayman (the latter, the present inventor) (C. V. Mosby Company 1978), summarizes the developments in the field and also describes many of the different types of devices which have been implanted in the past.

Although contrary to early efforts, placement of a device in the posterior chamber has a number of substantial advantages. Accordingly, in recent years several devices have been proposed and developed for placement in that chamber. The Shearing intra-ocular lens, which is described in U.S. Pat. No. 4,159,546, uses a pair of spring-like loops on either side of the lens (optic) which are positioned in the area between the iris and the ciliary body known as the ciliary sulcus. The Shearing lens is plano-convex with the plane surface designed to contact the posterior capsule or surface of the natural lens, which membrane is normally left intact but often perforated (discissed), during extracapsular cataract extraction (ECCE). The optic portion of the Shearing lens is circular. The Shearing lens is similar in construction to an earlier device of Barraquer, but which was designed for placement in the anterior chamber. The patents to Poler U.S. Pat. No. 4,073,014 and 4,080,709 are other examples of posterior chamber devices.

The present invention relates to a unique implantable intra-ocular device having a number of substantial advantages over prior art devices, including the device of Shearing. As in Shearing, in the present invention two haptic loops are attached to a lens, opposite each other. As in Shearing, at least one of the haptic loops is compressable, and preferably both can be compressed. Though the lens is designed for fixation in the ciliary sulcus, the unique compressability of the haptic loops achieved by using dissimilar thicknesses in the upper and lower loops make the present invention also suitable for insertion in the capsular "bag", (this is the remmant of the capsule of the natural lens, after extracapsular cataract extraction). However, in contrast to Shearing the lower loop has a stiffness greater than that of the upper loop. The experience has been that when an implantable device displaces from its desired position, it tends to move downward, of if the pupil is assymetric the latter tends to peak upwards. Providing the lower haptic loop with a greater stiffness ensures that the device will remain in a proper position, and the optic will occupy all or most of the pupillary aperture.

The lens of the present invention has a vertical dimension greater than its horizontal dimension. Since decentering as noted above tends to be movement in the vertical direction, making that dimension greater also helps ensure that the lens will be maintained in a position to satisfactorily carry out its function.

Implantation can either take place at the time the cataract is removed, i.e., primary implantation, or during a second operation subsequent thereto, i.e., secondary implantation. As noted above, during ECCE the posterior capsule or surface of the natural lens is usually left intact, but is often perforated to guard against the possibility that it will later become opaque. If that occurs the perforation will allow a distinct image to impinge on the retina to provide satisfactory vision. This step of perforation is called discission. During primary implantation the normal procedure is to carry out discission after the implanted lens has been put in place. After the nucleus and cortex of the natural lens has been removed, the pressure of the vitreous fluid behind the natural lens capsule often pushes that posterior surface forward. In the Shearing lens, the membrane presses directly against the plane rear surface of the lens, which can make discission a difficult operation without decentering the lens and/or getting vitreous fluid into the anterior chamber.

This problem however is much reduced by the present invention in which the rear surface of the lens is convex, providing sufficient room to carry out discission without difficulty. In addition, the optical characteristics of the lens of the present invention are believed to be improved by making the rear surface convex and the front surface plano.

According to another aspect of the present invention, the front surface of the lens is provided with at least one, and preferably upper and lower, angulated bores which extend into the lens at an angle to the vertical of, for example, 15° to 20°. In the past it has been conventional to insert the device into the eye using forceps. However, opening forceps in the limited space within the anterior chamber can be disadvantageous to the corneal endothelium. By providing angulated bores, the implant can be fixated at either the upper or lower angulated bore with either a fine spatula or forceps and maneuvered interiorly into position.

According to another aspect of the invention, the lens is provided with straight line portions in the lateral edges of the optic. These straight edges not only minimize the incision required to insert the implant but also guide the lens into position as it is inserted. Lenses having a circular shape, such as the Shearing lense, may have some tendency to go off center during insertion, as their maximum diameter clears the incision internally.

To implant the device of the present invention, an air bubble (or other substance to form the anterior chamber) is usually placed in the anterior chamber and the device slid into the chamber behind the bubble through a cornealscleral incision. The device is then moved inferiorly so that the lower loop compresses in the inferior (lower) ciliary sulcus. Inferior movement can then be continued with the lower loop compressed until the upper loop clears the pupillary margin. If necessary to clear the margin, the upper loop can also be compressed using a second instrument, or the upper iris can be retracted. When the implant is released, the device springs into place and will be held without suturing, (though a suture can be used through the upper loop). An angulated bore is preferably provided in the lens for permitting ready manipulation of the lens within the eye with a fine spatula or other instrument. The device of the present invention can be implanted with relative ease by either a right or a left-handed surgeon.

Other objects and purposes of the invention will become clear from the following detailed description of the drawings.

BRIEF DESCRIPTION OF THE DRAWINGS

FIG. 3 shows a schematic view of the device of the present invention being inserted into the anterior chamber through an appropriate incision, after an extracapsular cataract extraction.

FIG. 4 shows a further schematic view of the present invention with the lower haptic loop being compressed in the inferior ciliary sulcus by a spatula or similar instrument engaging the upper angulated bore.

FIG. 5 shows a schematic view of the present invention with the implant moved inferiorly behind the pupillary margin.

FIG. 6 shows a schematic view of the present invention with the implant sprung into the desired position behind the iris with the loops in the ciliary sulcus and the discission being carried out behind the lens.

DETAILED DESCRIPTION OF THE DRAWINGS

Figure 1:
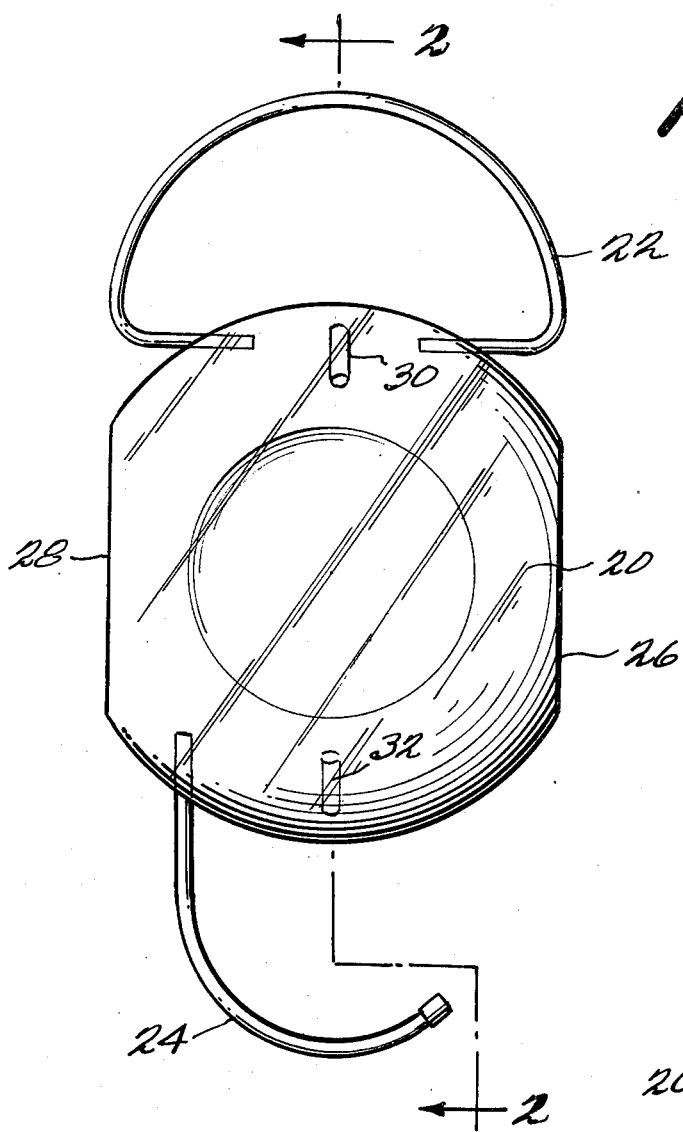
FIG. 1 shows a front view of the device of the present invention.
Figure 2:
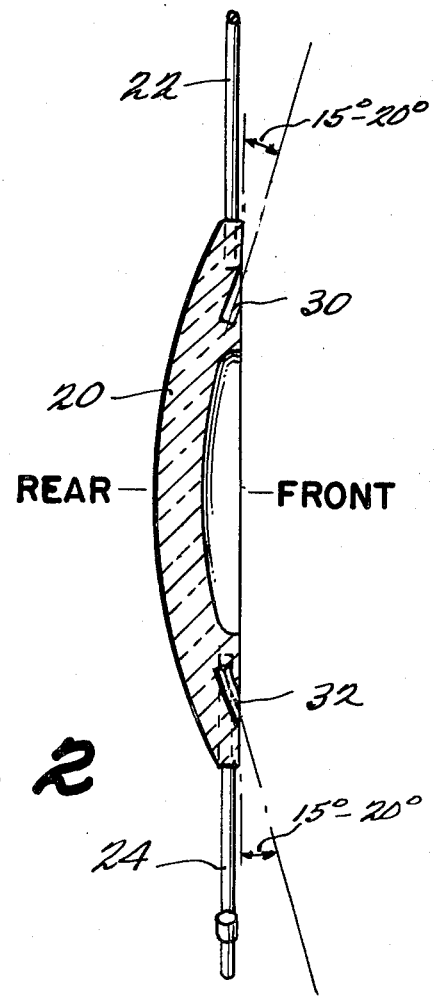
FIG. 2 shows a side view of the device of the present invention.

Reference is now made to FIG. 1 and to FIG. 2 which show respectively front and side views of the present invention. The device of the present invention is comprised of an ovoid shaped lens 20 of suitable material, upper haptic loop 22 attached to lens 20 and lower haptic loop 24 also attached to lens 20. The two haptic loops may be inserted into drill holes or molded with the optic and are fixed in place at the periphery of lens 20 opposite each other. The edge of the lens between the two loops includes straight lines portions 26 and 28 which, as noted above, aid in guiding the lens into position through a small incision. The lower haptic loop 24 acts like a spring during insertion of the device as explained in detail below. Angulated bores 30 and 32 are provided in the front surface of lens 20 for fixating the device to a fine spatula or other similar instrument to properly insert and position the lens, avoiding trauma to the corneal endothelium. An angle of 15° to 20° to the vertical is believed satisfactory.

The lower loop 24 has a greater stiffness than upper loop 22 to ensure the lens centers after insertion. This differential stiffness can, for example, be provided by making the upper loop of 5-0 polypropylene or nylon and the lower loop of 4-0 polypropylene or nylon or other bio-acceptable material. Since displacement after implantation when it occurs is usually vertical, acceptable optical function is also enhanced by making the lense ovoid with a vertical dimension greater than its horizontal dimension, thus occupying the pupillary aperture with the lens optic.

Upper loop 22 is preferably closed by being fixed at both ends, unlike the Shearing device, to have the greater strength which results from two points of fixation. In addition, closed upper loop 22 can be sutured in place, if the surgeon desires.

To aid in discission, the rear optic surface of the lens 20 which contacts the capsule which is the rear surface of the natural lens of the eye is convex rather than plano. The front surface of the optic is essentially plano and this plano-convex configuration is belived to have superior optical characteristics.

Lens 20 is preferably formed of a suitable plastic such as polymethylmethacrylate or glass and may be made either by injection or compression molding or lathe cutting or any other techniques (or a combination) using conventional techniques for making lenses for intraocular implantation.

FIGS. 3 through 6 show schematically the surgical procedure for inserting the present device. Referring to the FIG. 3, the device of the present invention is slipped through the incision into the anterior chamber by a suitable forceps under an air bubble which has been previously provided. Referring to FIG. 4, the implant is then fixated at the upper angulated bore hole 30 with a fine spatula or other similar instrument and maneuvered inferiorly until the lower loop 24 compresses against the inferior ciliary sulcus in the posterior chamber. The lower bore hole permits insertion upside down from the illustrated and preferred technique if desired by the surgeon. As shown in FIG. 4, lower loop 24 is compressed until the upper loop 22 clears the pupillary margin. If necessary, the upper loop can also be compressed by a second instrument to clear the pupillary margin and/or the iris can be retracted. The implant can then be released as shown in FIG. 5 to spring behind the iris due to the resiliency inherent in the lower loop 24, the forces applied by the spatula and the balloting effect of the air bubble. The spatula can then be withdrawn. After the implant has sprung into the desired position behind the iris and in the ciliary sulus, the pupil can be constricted by suitable means and a peripheral iridectomy (removal of part of the iris) may be performed. If desired, the upper loop can be sutured to provide a fixed anchor. At this point as shown in FIG. 6 a discission may be performed to obviate late opacification of the posterior capsule. The wound can now be sutured and the procedure terminated.

Many changes in modification in the above described embodiment of the invention can, of course, be carried out without departing from the scope thereof. Accordingly, that scope is intended to be limited only by the scope of the appended claims.

What is claimed is:

1. An intra-ocular device for implantation in the posterior chamber of an eye comprising:

a lens having a dimension in one transverse direction across the lens surface greater than its dimension in a perpendicular direction across the lens surface, upper and lower haptic loops attached to said lens on opposing sides thereof, for contacting the eye surface in the posterior chamber to position said lens in the posterior chamber.

2. An intra-ocular device for implantation in the posterior chamber of an eye as in claim 1, wherein said lens has front and rear surfaces with at least one bore extending at an angle to the vertical dimension of said lens less than 90° for fixating upon a spatula or similar instrument during implantation in an eye.

3. A device as in claims 1 or 2 wherein the edge of said lens between said loops include lateral straight line portions.

4. A device as in claims 1 or 2 wherein said upper loop is fixed to said lens at both ends and said lower loop is compressable and fixed to said lens at only one end.

5. A device as in claims 1 or 2 wherein the lower loop has a stiffness greater than the upper loop.

6. A devivce as in claims 1 or 2 wherein said lens has front and rear surfaces, the rear surface being convex and the front surface being plano.

7. A device as in claim 1 or 2 wherein said lens has a dimension in the vertical direction greater than its dimension in the horizontal direction.

8. A device as in claim 2 wherein first and second bores are provided.

9. A device as in claim 2 wherein said bores extend at an angle of substantially 15° to 20° to the vertical.

10. An intra-ocular device for implantation in the posterior chamber of an eye comprising:

an ovoid shaped lens having a vertical dimension greater than its horizontal dimension, upper and lower angulated bore holes adjacent the upper and lower edges of the lens, each hole extending at acute angle to the vertical, and a convex rear surface, and upper and lower haptic loops respectively fixed to said lens adjacent the upper and lower edges, at least one of said loops being compressable, and the lower loop having a stiffness greater than that of the upper loop for maintaining said lens in position after implantation.

11. A device as in claim 10 wherein both said loops are compressable, said upper loop is fixed at both ends to said lens and said lower loop is fixed at only one end to said lens.

12. A device as in claim 10 wherein the front surface of said lens is plano.

13. A device as in claim 10 wherein the peripheral portion of said lens between said loops includes lateral straight edge portions.

* * * * *

＃ REEXAMINATION CERTIFICATE (1524th)

United States Patent [19]

Clayman

[11] B1 4,298,994

[45] Certificate Issued    Aug. 6, 1991

[ ] POSTERIOR CHAMBER INTRA-OCULAR TRANSPLANT DEVICE

[ ] Inventor: Henry M. Clayman, 13255 Biscayne Bay Dr., Miami, Fla. 33181

Reexamination Request:
No. 90/002,110, Aug. 17, 1990

Reexamination Certificate for:
Patent No.: 4,298,994
Issued: Nov. 10, 1981
Appl. No.: 88,643
Filed: Oct. 26, 1979

Int. Cl.$^5$ .............................................. A61F 2/16
U.S. Cl. ....................................................... 623/6
Field of Search .......................................... 623/6

References Cited

U.S. PATENT DOCUMENTS

| | | |
|---|---|---|
| 3,866,249 | 2/1975 | Flom . |
| 3,913,148 | 10/1975 | Potthast . |
| 3,922,728 | 12/1975 | Krasnov . |
| 4,056,855 | 11/1977 | Kelman . |
| 4,073,014 | 2/1978 | Poler . |
| 4,087,866 | 5/1978 | Choyce . |
| 4,092,743 | 6/1978 | Kelman . |
| 4,159,546 | 7/1979 | Shearing . |
| 4,174,543 | 11/1979 | Kelman . |
| 4,214,585 | 7/1980 | Bailey, Jr. . |
| 4,242,760 | 1/1981 | Rainin ................................. 623/6 |
| 4,251,887 | 2/1981 | Anis ..................................... 623/6 |

FOREIGN PATENT DOCUMENTS

| | | |
|---|---|---|
| 959314 | 3/1957 | Fed. Rep. of Germany . |
| 1103399 | 5/1955 | France . |
| 563174 | 7/1977 | U.S.S.R. . |
| 2046099 | 11/1980 | United Kingdom . |

OTHER PUBLICATIONS

J. F. Worst, M.D., Haren, Holland, Iris Claw Lens, Intra-Ocular Implant Soc. J–vol. 6, Apr. 1980.
Search Report/Patent Cooperation Treaty, dated 2/81 for PCT/US81/01256 filed 9/18/81.
Copy of European Supplementary Search Report dated 5/85; 3 pages.
American Intra-Ocular Implant Society Journal, vol. No. 3, Jul. 1978 (The EYE AP.PEELING aspect of dry pack . . . .
Photograph of Medallion circular loop lens—Intracapsular extraction (Clipfixation or Suturefixation (remove )).
Photograph of Medallion small incision lens—for secondary implantion (Secondary Implantation (f.i. after phakoemulsification)).
Photograph of Medallion two-loop lens (Intracapsular extraction Extracapsular extraction Suturefixation).
Photograph of a Worst Lobster Claw Lens.
Boberg-Ans, J., "Experience with Twelve Cases of Intra-Ocular Anterior Chamber Implants for Aphakia: Two New Models of Lens are Described"; Brit. J. Ophthal. (1961) 45, 37.
Jaffe, Norman S., et al., Pseudophakos, C. V. Mosby Company, St. Louis (1978) pp. 35–41.
Choyce, Peter, Intra-Ocular Lenses and Implants, H. K. Lewis & Co., Ltd., London (1964), pp. 12–13.
"Kelman Type II Anterior Chamber Intraocular Lens" (brochure), Precision-Cosmet Co., Inc., Minneapolis (Oct. 1978).
Shearing, Steven P., "Complications of Shearing Posterior Chamber Intraocular Lens", Contact and Intraocular Lens Medical Journal, vol. 5, No. 2, pp. 64–74, Apr.-/Jun. 1979.
Shearing, Steven P., "A Practical Posterior Chamber Lens", Contact and Intraocular Lens Medical Journal, vol. 4, No. 3, pp. 114–119, Jul./Sep. 1978.
Nordlohne, M. E., The Intraocular Implant Lens Development and Results with Special Reference to the Binkhorst Lens. Dr. W. Junk B.V., Pub., The Hague (1975), pp. 14–25.
Deposition of Henry M. Clayman, M.D., vol. II, pp. 83–91, Jan. 27, 1990 in Civil Action No. C88-1377R in the U.S. Dist. Ct., West Dist. of Washington at Seattle.
Jalie, M., The Design of Intra-Ocular Lenses (article), British Optical Association, Publishers (May 1978), pp. 1–21.
Tennant, Jerald L., A Lens for All Seasons (1976), pp. 46–51, 62–63, 66–67.

Primary Examiner—Clifford D. Crowder

[57]    ABSTRACT

An intra-ocular implantable device and a method of surgically implanting such device in which upper and lower haptic loops are attached to a lens on opposite sides thereof for contacting the ciliary sulcus (or capsular bag) to position the lens in the posterior chamber. The lower loop has a stiffness greater than the upper loop and the lens has a vertical dimension greater than its horizontal dimension to ensure proper positioning of the lens. The lens has a rear convex surface for facilitating discission after implantation and optical advantages. Upper and lower bores in the front surface of the lens extend at an angle to the vertical of, for example, 15° to 20° to permit fixation by a fine spatula for manipulation of the device during implantation. The edges of the lens between the loops include straight line portions for guiding the device during insertion and requiring minimum incision.

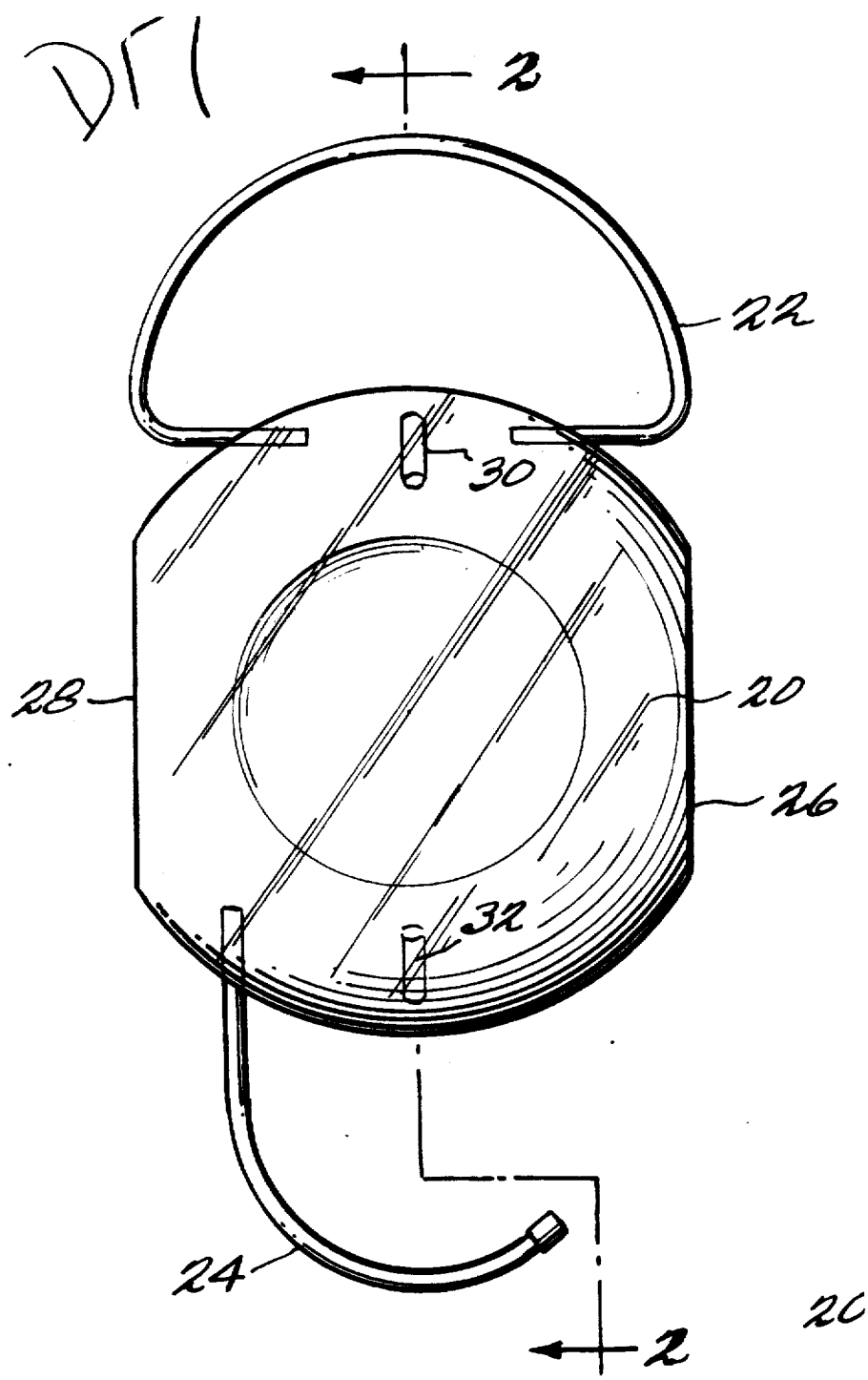

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-13 is confirmed.

New claims 14-18 are added and determined to be patentable.

*14. An intra-ocular device for implantation in the posterior chamber of an eye comprising:*
  *a lens having a dimension in one transverse direction across the optic greater than its dimension in a perpendicular direction across the optic; and*
  *upper and lower haptic loops attached to said lens on opposing sides thereof, for contacting the eye surface in the posterior chamber to position said lens in the posterior chamber.*

*15. A device as in claim 14 wherein said greater of said dimensions is substantially in the direction in which said haptic loops extend.*

*16. An intra-ocular device for implantation in the posterior chamber of an eye comprising:*
  *a lens having a dimension in one transverse direction across the optic greater than its dimension in a perpendicular direction across the optic; and*
  *upper and lower haptic loops attached to said lens on opposing sides thereof, for contacting the eye surface in the posterior chamber to position said lens in the posterior chamber, the greater of said dimensions being substantially in the direction in which said haptic loops extend.*

*17. An intra-ocular device for implantation in the posterior chamber of an eye comprising:*
  *a lens having a vertical dimension greater than its horizontal dimension and front and rear optical surfaces bounded by upper and lower edges; and*
  *upper and lower haptic loops respectively fixed to said lens adjacent the upper and lower edges, said loops being compressible for maintaining said lens in position after implantation.*

*18. An intraocular device for implantation in the eye comprising:*
  *a posterior chamber lens having a dimension across the lens surface greater than its dimension in a perpendicular direction across the lens surface; and*
  *upper and lower haptic loops attached to said lens on opposite sides thereof, for contacting the eye surface in the posterior chamber to position said lens in the posterior chamber.*

* * * * *